United States Patent [19]
Besnier

[11] Patent Number: 5,531,964
[45] Date of Patent: Jul. 2, 1996

[54] AUTOMATED ANALYSIS CHAIN

[75] Inventor: Joseph Besnier, Acqueville, France

[73] Assignee: Compagnie Generale Des Matieres Nucleaires, Velizy-Villacoublay, France

[21] Appl. No.: 328,802

[22] Filed: Oct. 25, 1994

[51] Int. Cl.⁶ .......................... G01N 35/02; G01N 35/04
[52] U.S. Cl. ................. 422/63; 422/65; 422/67; 422/68.1; 422/71; 436/47; 436/48; 436/49; 436/57; 376/245; 73/864.21
[58] Field of Search .................. 422/62–67, 71, 422/900, 902; 436/57, 804, 47, 48, 49; 73/864.21, 864.22, 864.23, 864.24, 863.83; 376/245

[56] References Cited

U.S. PATENT DOCUMENTS

| | | | |
|---|---|---|---|
| 3,481,709 | 12/1969 | Slone | 422/66 |
| 3,986,835 | 10/1976 | Takagi | 422/71 |
| 4,229,864 | 10/1980 | Berger et al. | |
| 4,470,265 | 9/1984 | Correia | 62/77 |
| 4,766,550 | 8/1988 | Byers et al. | 422/62 |
| 4,781,891 | 11/1988 | Galle et al. | 422/64 |
| 4,853,546 | 8/1989 | Abe et al. | 250/432 |
| 4,854,355 | 8/1989 | Chazot et al. | |
| 5,102,623 | 4/1992 | Yamamoto et al. | 422/63 |
| 5,173,741 | 12/1992 | Wakatake | 356/246 |
| 5,176,880 | 1/1993 | Iwasaki et al. | 422/63 |
| 5,245,530 | 9/1993 | Taki | 364/167.01 |
| 5,270,006 | 12/1993 | Uchigaki et al. | 422/63 |
| 5,279,337 | 1/1994 | Ringot et al. | |
| 5,280,140 | 1/1994 | Besnier et al. | |
| 5,314,662 | 5/1994 | Hemzy et al. | 422/62 |
| 5,318,359 | 6/1994 | Wakatake | 366/140 |
| 5,328,662 | 7/1994 | Ringot et al. | 422/63 |
| 5,366,896 | 11/1994 | Margrey et al. | 436/48 |

FOREIGN PATENT DOCUMENTS

| | | |
|---|---|---|
| 0003936 | 9/1979 | European Pat. Off. . |
| 0286536 | 10/1988 | European Pat. Off. . |
| 0364078 | 4/1990 | European Pat. Off. . |
| 0509919 | 10/1992 | European Pat. Off. . |
| 0522959 | 1/1993 | European Pat. Off. . |
| 0557828 | 9/1993 | European Pat. Off. . |
| 2675902 | 4/1991 | France . |
| 2675582 | 4/1991 | France . |
| 2165048 | 4/1986 | United Kingdom . |

OTHER PUBLICATIONS

IEEE Transaction on Industry Applications—vol. 28, No. 4, Aug. 1992, New York US, pp. 938–944—Gecks "Robotics an efficient tool for laboratory automation".
Chemometrics, vol. 21, No. 2–3, Dec. 1993, NL, pp. 207–214—Bengelsdijk et al. "Standard laboratory module".
Patent Abstracts of Japan—vol. 4, No. 10 (P–022) Aug. 8, 1980 & JP 55 066 758.
Patent Abstracts of Japan—vol. 17, No. 157 (P–1511) Mar. 26, 1993 & JP 04 323 562.

*Primary Examiner*—Jill Warden
*Assistant Examiner*—Harold Y. Pyon
*Attorney, Agent, or Firm*—Pearne, Gordon, McCoy & Granger

[57] ABSTRACT

In order to reduce liquid effluents and solid waste in an analysis chain receiving liquid samples contained in jugs (16), the proposal is to automate all the operations performed in analysis units or boxes (10a, 10b). Moreover, when the sampling operations necessary for the analyses have been carried out in the analysis units (10a, 10b), the jugs can be automatically dispatched to a recycling apparatus (52).

8 Claims, 1 Drawing Sheet

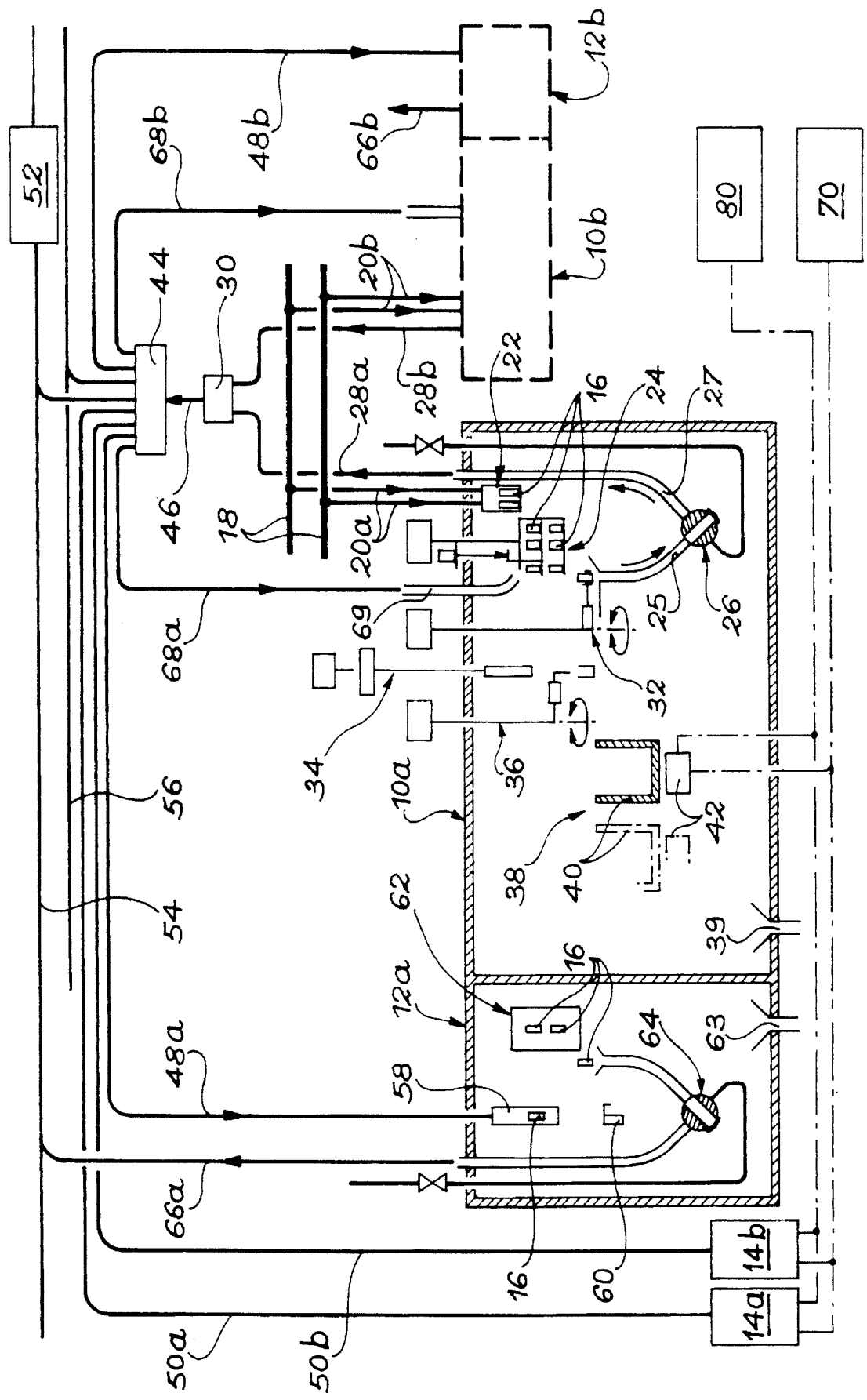

AUTOMATED ANALYSIS CHAIN

BACKGROUND OF THE INVENTION

The invention relates to an analysis chain or line designed for performing in an automated manner analyses, such as chemical analyses, on liquid samples contained in jugs.

Such an analysis chain can in particular be used in the nuclear industry for periodically checking the characteristics of certain products in a production or reprocessing plant without causing any risk for personnel or for the environment.

FR-A-2 675 582 describes an automated installation making it possible to take liquid samples at different points of a nuclear plant, introduce the samples into jugs and transfer the latter into analysis units or boxes by means of a pneumatic transfer system controlled by a central control unit.

FR-A-2 675 902 describes a device usable in such an automated installation for taking liquid samples and automatically introducing them into sealed jugs permitting their transfer to analysis units.

The existing installations, more particularly illustrated by the aforementioned documents, permit the automatic performance of sampling operations and the transfer of the jugs into the analysis units. However, the different operations which are then performed within the analysis units are carried out manually with the aid of remote handling grippers or tongs by operators located behind the windows equipping the analysis units. The protection of the personnel is ensured both by a complete sealing of the analysis units, which prevents the migration of contamination to the outside, and by shields protecting personnel against irradiation.

However, the manual performance of the different operations which have to be carried out in such analysis units causes numerous disadvantages which will now be described.

A first disadvantage relates to the identification of the jugs. Thus, the identification takes place by the operator through a very thick and therefore highly deforming window. Moreover, the identification relates to jugs which drop loosely into the bottom of the analysis unit when they reach the latter. This problem leads to an error risk and even to the loss of certain jugs. This often leads to operators requesting supplementary jugs and therefore increases the quantities of liquid and solid waste.

Another disadvantage relates to the unsealing of the jugs with the aid of remote manipulation grippers. This operation is particularly difficult and leads to a loss of time and to a risk of the content being poured into the bottom of the analysis unit.

It is also impossible to reseal the jugs with the aid of grippers in the analysis unit. Consequently it is impossible to recover surplus liquid samples or this can only be envisaged by creating a costly and complicated gravity collection system within the framework of existing equipment.

Other disadvantages result from the use of a conventional laboratory pipette for taking the samples necessary for analyses from the jugs. Thus, this procedure involves taking for each analysis a relatively large liquid quantity (at least 2 ml), which leads to a large liquid effluent volume. In addition, it is virtually impossible to perform several analyses on the basis of the same jug, which also considerably increases the quantities of solid and liquid waste. Moreover, a large quantity of chemical reagents is used, which increases operating costs. Finally, the analytical chemical reagents constitute disturbing ions, whose large quantity is very prejudicial with respect to the treatment of the effluents and/or a possible recycling.

SUMMARY OF THE INVENTION

The invention specifically relates to an analysis chain, whose design makes it possible to reduce the quantity of solid waste, reduce the liquid effluent quantity and increase productivity, while retaining the existing analysis units and while maintaining the double radiological confinement of said units.

According to the invention, this result is obtained by means of an automated analysis chain comprising:

at least one analysis unit able to receive sealed jugs containing a liquid to be analyzed;

a pneumatic transfer system able to automatically transfer the jugs into the analysis unit; and a central control unit controlling the pneumatic transfer system;

characterized in that each analysis unit has automated processing means, controlled by the central control unit, for opening the jugs, taking samples therefrom, analyzing these samples and resealing the jugs, as well as first means for redespatching the jugs to the pneumatic transfer system.

The automation of the operations performed within each analysis unit makes it possible to eliminate all the disadvantages resulting from the manual performance of these operations in existing installations. It should be noted that the automated sealing and unsealing of the jugs are facilitated by using jugs with screw caps.

Preferably, each of the analysis units also has jug storage means controlled by the central control unit and provided with an ejection station directly communicating with the first means for the redespatch of the jugs. Moreover, the processing means incorporate gripping means able to take and then reintroduce the Jugs at the exit from the ejection station. These characteristics make it possible to store in each analysis unit both jugs which are to undergo analyses within the unit and jugs which are to be directly redespatched to existing equipments.

Advantageously, each analysis unit also has means for the automatic weighing of the jugs when they enter the analysis unit and sorting means controlled by the central control unit in response to signals supplied by the weighing means and able to automatically introduce full jugs into the storage means and eliminate empty jugs, e.g. by allowing them to fall into the bottom of the analysis unit or, preferably, by redespatching them to a jug destruction unit.

The analysis chain can also comprise at least one non-destructive measuring apparatus, such as a physical measuring apparatus connected by the pneumatic transfer system to the first means for redespatching the Jugs and to a direct supply station for the storage means equipping each analysis unit.

An apparatus for the recycling of liquid remaining in the jugs is advantageously provided, the apparatus being connected by the pneumatic transfer system to the first means for redespatching the jugs.

Preferably, the pneumatic transfer system comprises means for switching the jugs, able to alternately direct the jugs coming from the first means in order to redespatch the jugs to the recycling apparatus and to the non-destructive measuring apparatus and able to alternately direct the Jugs coming from the non-destructive measuring apparatus to the direct supply station and to the recycling apparatus.

As a result of these features, it is possible to perform analyses and measurements of a non-destructive nature in this order or in the reverse order for each of the jugs.

The analysis chain can also comprise at least one manual analysis unit having means for opening and closing the jugs and second means for redespatching the jugs into the pneumatic transfer system.

In the latter case, the switching means are also able to direct the jugs from the first means in order to redespatch the jugs to the manual analysis unit. Preferably, the manual analysis unit also has means for washing and rinsing the jugs.

BRIEF DESCRIPTION OF THE DRAWING

A description will now be given in non-limitative manner of a preferred embodiment of the invention with reference to the single drawing, which diagrammatically shows an automated analysis chain according to the invention having two automatic analysis units, two manual analysis units and two non-destructive measuring apparatuses.

DETAILED DESCRIPTION OF THE PREFERRED EMBODIMENT

In the single drawing, the references 10a and 10b designate two automatic analysis units having an identical configuration and reference numerals 12a and 12b designate two manual analysis units, also having an identical configuration and respectively associated with the automatic analysis units 10a and 10b.

The automatic analysis units 10a, 10b, as well as the manual analysis units 12a, 12b have confinement enclosures ensuring a complete seal with respect to the migration of contamination to the exterior. These enclosures are surrounded by an e.g. lead shielding, which protects personnel against irradiation.

The analyses performed in the automatic analysis units 10a, 10b are chemical analyses, which are carried out automatically. However, the analyses performed in the manual analysis units 12a, 12b are chemical analyses, whose performance is not or cannot be automated. The analyses performed in the analysis units 10a, 12a on the one hand and analysis units 12b on the other can be identical or different, as a function of the envisaged application.

The analysis chain or line illustrated in the single drawing also comprises two apparatuses 14a, 14b making it possible to perform non-destructive measurements such as physical measurements. These non-destructive measurements are generally physical measurements of different natures.

The analyses performed in the automatic units 10a, 10b and manual units 12a, 12b, as well as the measurements performed in the non-destructive apparatuses 14a, 14b concern liquid samples taken at one or more points of a nuclear plant, such as a fuel reprocessing plant. These sampling operations can in particular be carried out by installations like those described in FR-A-2 675 902. The liquid samples taken are introduced by the installations into the jugs 16. The latter are tight containers sealed by a screw cap and whose cylindrical shape is intended to permit their transfer from one point to another within the chain by a pneumatic transfer system, whose general design is identical to that of FR-A-2 675 582.

This pneumatic transfer system firstly comprises an upstream part, by which all the jugs 16 coming from the liquid sampling installations are passed to one or other of the automatic analysis units 10a, 10b. In the drawing the upstream part of the pneumatic transfer system is illustrated by two main pipes 18, connected to the not shown sampling installations, and by branch pipes 20a, 20b by which each of the main pipes 18 is respectively connected to the automatic analysis unit 10a and to the automatic analysis unit 10b. Not shown, switching mechanisms, e.g. of the drum or slide type, make it possible to direct the jugs circulating in the main pipes 18 to the branch pipes 20a or 20b, as a function of the nature of the analyses to be carried out or as a function of the overall dimensions of the automatic analysis units 10a, 10b.

The internal fitting of the automatic analysis unit 10b is the same as that of the automatic analysis unit 10a, so that only the fitting of the latter will be described.

On entering the automatic analysis unit 10a, the jugs 16 introduced by the branch pipes 20a drop by gravity onto automatic weighing means 22, in a manner comparable to that described in FR-A-2 675 582. When each jug 16 arrives, the automatic weighing means 22 emit a signal representative of the jug weight. The comparison of this signal with a predetermined threshold consequently makes it possible to know if the jug 16 introduced into the automatic analysis unit 10a is full or empty.

According to the results of this comparison, not shown sorting means associated with the automatic weighing means 22 make it possible either to introduce the jug 16 into a buffer storage device 24 if it is full, or eliminate the jug if it is empty. The sorting means can redespatch empty jugs to a jug destruction apparatus or eject them into the bottom of the automatic analysis unit 10a. In the latter case, the automaton of a control station 80, which controls the entire chain, commands a supplementary sampling operation in the corresponding sampling installation in order to compensate the defective sampling operation and also alerts the operator.

The sorting means which are associated with the automatic weighing means 22 are advantageously constituted by two pneumatic ejectors oriented in different ways, in order to move the jug either into the buffer storage device 24 or into the bottom of the automatic analysis unit 10a.

The buffer storage device 24 is constituted by a modular assembly having one or more stages and incorporating e.g. a rotary drum peripherally provided with cavities. More specifically, these cavities can be radially open towards the outside in order that a Jug 16 can be introduced into the same under the action of a compressed air jet when it is positioned facing a cavity. Mechanisms, advantageously located outside the automatic analysis unit 10a, control the stepwise rotation of the drum and optionally its rise and fall when the buffer storage device 24 has several levels.

The ejection of jugs 16 out of the buffer storage device 24 also takes place radially to the outside, e.g. with the aid of a mechanism controlled by a jack positioned outside the automatic analysis unit 10a. This ejection takes place at a fixed station or location known as the ejection station.

This ejection station communicates directly with the means 26 in order to redespatch the Jugs 16 into the pneumatic transfer system outside the automatic analysis unit 10a. More specifically, a jug ejected at the ejection station of the buffer storage device 24 is positioned above the mouth of an intake chute 25, by which said jug can drop by gravity into the jug redespatch means 26.

These means 26 for the redespatch of the Jugs can in particular comprise a rotary sleeve, equipped with a receptacle which can be placed either in the extension of the aforementioned intake chute 25, or in the extension of an outlet tube 27 traversing the enclosure of the automatic analysis unit 10a and connected to the pneumatic transfer system outside said enclosure. In the latter position, the redespatch of the jug takes place pneumatically. Outside the analysis unit, the outlet tube 27 is extended by a tube 28a of the pneumatic transfer system for the automatic analysis unit 10a and by a tube 28b for the automatic analysis unit 10b. The tubes 28a, 28b are connected to a mechanical switching system 30.

Although the ejection station of the buffer storage device 24 makes it possible to directly evacuate the jugs 16 out of the automatic analysis unit 10a by the jug redespatch means 26, most of them do not have to follow this direct path. Thus, the liquid which they contain must undergo one or more analyses within the automatic analysis unit 10a. Therefore, for this purpose, the latter is equipped with automated treatment or processing means, including a gripping module 32 making it possible to take samples from the jugs 16 during their ejection from the buffer storage device 24 instead of them dropping by gravity into the intake chute 25 of the jug redespatch means 26.

This gripping module 32 can in particular be constituted by a gripping tongs equipped with a retractable bottom and which can be horizontally moved between a gripping station and a working station. When it occupies the gripping station, the tongs are positioned vertically of the ejection station for the buffer storage device 24 and immediately above the intake chute 25 for the jug redespatch means 26.

In the work station of the gripping tongs, the processing means equipping the automatic analysis unit 10a make it possible to open the jugs 16 placed in said tongs by unscrewing the cover forming a cap, perform one or more sampling operations and then screw down the cover again in order to reseal the jug before redespatching it outside the automatic analysis unit 10a.

For this purpose, the processing means equipping the automatic analysis unit 10a incorporate, apart from the gripping module 32, a module 34 for screwing down/unscrewing the cap equipping the jugs 16 and a module 36 for taking liquid samples from the jug. To these modules is added an analysis installation 38.

The module 34 for screwing down/unscrewing the cap can in particular be equipped with a gripper which can lock the cap of a jug held by the gripping module 32. A rotation of said gripper in either direction makes it possible to respectively screw down and unscrew the cap. A vertical displacement of the gripper between a bottom screwing down position and an upper unscrewing position permits, in said latter position, the freeing of a space above the unsealed jug 16, so that one or more liquid sampling operations can be carried out by the sampling module 36.

In turn, the sampling module 36 can be equipped with a suction end fitting connected to a piston pump through a hydraulic guard. This end fitting can be vertically displaced in order that it can be lowered into the jug held by the gripping module 32 and horizontally so that it can be brought from the station in which the sampling operation takes place to a station in which the sample taken is delivered to the receptacle 40 of the analysis apparatus 38.

The mechanisms controlling the modules 32, 34, 36 are advantageously at least partly located outside the automatic analysis unit 10a.

The automatic analysis apparatus 38 can comprise one or more cups or cells 40 arranged so as to be able to receive a liquid sample to be analyzed, as well as reagents and possible catalysts. In the case where the automatic analysis apparatus 38 comprises several cups 40, the latter can be installed on a rotary plate or positioned at fixed locations above which can be successively placed the suction end fitting of the sampling module 36.

The analysis apparatus 38 is provided with not shown, automated systems making it possible to inject the reagents and catalysts into each of the cups 40 and empty the cups and rinse them after each analysis. An e.g. magnetic stirrer is also placed in each cup 40. In addition, the analysis apparatus 38 has instruments making it possible to perform the measurements corresponding to the analyses to be carried out. The instruments associated with each cup 40 are diagrammatically illustrated by the blocks 42 in the drawing. They are controlled by the automaton of the control station 80, as are the treatment and processing means equipping the automatic analysis units 10a, 10b. Therefore the samples can in each case be kept without any risk of error and the repeatability of the analyses is ensured.

Apart from the tubes 28a, 28b and the switching system 30 to which said tubes are connected, the part of the pneumatic transfer system downstream of the automatic analysis units 10a, 10b has a second mechanical switching system 44 downstream of the switching system 30 and connected to the latter by a tube 46. The switching system 44, which is in practice in the form of a drum, makes it possible to despatch as required the jugs 16 passing out of the automatic analysis units 10a, 10b either to the manual analysis units 12a, 12b by the tubes 48a, 48b, or to the non-destructive measuring apparatuses 14a, 14b by tubes 50a, 50b, or to an apparatus 52 for recycling liquid remaining in the Jugs by a tube 54, or finally to another installation such as a laboratory by a tube 56.

The equipment internally equipping the manual analysis units 12a, 12b are identical, so that only that equipping the unit 12a will be described.

The jugs 16 despatched into the manual analysis unit 12a by the tube 48a enter said unit by a slip ring intake device 58, so that at all times the necessary seal of the manual analysis unit 12a is maintained. This intake device 58 is so designed that the jugs 16 drop automatically into the bottom of the manual analysis unit 12a.

When an operator wishes to carry out an analysis on the liquid contained in one of the Jugs introduced into the manual analysis unit 12a, he makes use of not shown handling grippers associated with the unit in order to seize the corresponding jug 16 and place it in a jug unsealing and resealing device 60. This device 60 can be identical to the screwing down/unscrewing module 34 equipping the automatic analysis units 10a, 10b. Preferably, it is a simplified, smaller device, whose control takes place manually with the aid of the handling grippers equipping the manual analysis unit 12a.

After opening the jug 16 in question, a sample is taken manually with the aid of grippers from the jug and the desired analysis is performed by the operator with the aid of appropriate, not shown means located for this purpose in the manual analysis unit 12a.

The cap of the Jug 16 is then screwed down again with the aid of the device 60 and the resealed jug is washed in a washing module 62 also located within the manual analysis unit 12a.

When washing is completed, the jug 16 is redespatched to the recycling apparatus 52 by the jug redespatch means 64. The latter are advantageously identical to the jug redespatch means 26 equipping the automatic analysis units 10a, 10b and are connected to the recycling apparatus 52 by a tube 66a, 66b connected to the tube 54 upstream of the apparatus 52.

The liquid effluents from the automatic analysis apparatuses 38 in the automatic analysis units 10a, 10b and the washing module 62 in the manual analysis units 12a, 12b are recovered by drain systems 39, 63 and are then treated. It is important to observe that the volume of the effluents is as small as possible, particularly for automatic analysis units. Thus, the volume is limited to the small volume sampled by the sampling modules 36, as well as the volumes corresponding to the reagents and the rinsing liquid.

When the jugs 16 are supplied to the non-destructive measuring apparatus 14a or 14b by the tubes 50a or 50b, the measurements are performed as soon as the jug in question enters the apparatus, without it being necessary to unscrew the cap. As soon as the corresponding measurement has been performed, the jug 16 is redespatched by the same tube 50a or 50b into the switching means 44. From the latter, the jug can be supplied either to the recycling apparatus 52 by the tube 54, or to another laboratory by the tube 56, or to one or other of the automatic analysis units 10a, 10b by the tubes 68a, 68b. These tubes 68a, 68b issue into each of the automatic analysis units 10a, 10b by a slip ring device 69 identical to the device 58 equipping the manual analysis units 12a, 12b.

More specifically, the slip ring devices 69 are positioned in such a way that the jugs 16 redespatched in this form into the automatic analysis units 10a, 10b are placed in the cavities of the buffer storage device 24 by appropriate means such as pneumatic ejectors. In combination with the switching means 44 and the buffer storage devices 24, the presence of the tubes 68a, 68b enables the automaton of the control station 80 to choose, for each of the jugs 16 penetrating the analysis units 10a, 10b by the branch pipes 20a, 20b, the order in which the chemical analyses and the non-destructive measurements is to be performed. Thus, the jugs 16 introduced into the buffer storage device 24 can either be sampled at the exit from said device by the gripping module 24 in order to undergo chemical analyses before being redespatched to the non-destructive measuring apparatuses 14a, 14b in order to undergo physical measurements, or despatched directly to said non-destructive measuring apparatuses by the jug redespatch means 26. In the latter case, the return of the jugs to the buffer storage device 24 by the tubes 68a, 68b makes it possible to then perform chemical analyses by taking samples from the jugs on leaving the buffer storage device with the aid of the gripping module 32. The sealed jugs 16, which are redespatched to the recycling apparatus 52 have therefore undergone the desired analyses and non-destructive measurements in the automatic analysis units 10a, 10b, in the manual analysis units 12a, 12b and/or in the non-destructive measuring apparatuses 14a, 14b. These jugs contain the residue of the liquid not used during the chemical analyses.

As is very diagrammatically illustrated by the drawing, all the modules equipping the automatic 10a, 10b and manual 12a, 12b analysis units, the non-destructive measuring apparatuses 14a, 4b, the recycling apparatus 52, as well as the pneumatic transfer system of the analysis chain according to the invention are 100% controlled by the automaton of the control station 80. As has already been stated, the automaton also controls the automatic analysis apparatuses 38 equipping the automatic analysis units. Consequently all the operations as from the departure of the jugs to the analysis apparatuses up to the complete analysis is automated and performed in chain form.

It should finally be noted that the automaton of the control station 80 controls all the operations of the automated chain through a data processing network making it possible to pass the digital and alphanumeric data such as curves from not shown computers associated with the different analysis apparatuses to a central control console 70 making it possible to follow and control all the operations.

I claim:

1. Automated analysis apparatus comprising:

at least one analysis box able to receive sealed containers containing a liquid to be analyzed;

a container transfer system including a tube network and air pressure transfer control means adapted to automatically transfer the containers into the analysis box via the tube network;

a central control unit controlling the transfer system; and wherein said analysis box comprises:

automated processing means controlled by the central control unit including means for opening the containers, sampling means for taking samples from open containers, analysis means for analyzing the samples, means for resealing the open containers, and first means for redespatching the containers to the transfer system;

container storage means controlled by the central control unit including an ejection station in communication with the first redespatching means; and said automated processing means further including means for gripping the containers at a location between the ejection station and the first redespatching means to transfer them to the opening means and gripping containers at the resealing means to transfer them to said location between the ejection station and the first redespatching means.

2. Analysis apparatus according to claim 1, wherein said analysis box further comprises:

means for automatically weighing the containers as they enter the analysis box, said automatic weighing means supplying to the central control unit signals representative of a weight of the container; and sorting means controlled by the central control unit for sorting the containers in response to the signals supplied by the weighing means, wherein full containers are introduced into the container storage means and empty containers are eliminated.

3. Analysis apparatus according to claim 1, further comprising at least one non-destructive measuring apparatus outside said analysis box for performing non-destructive measurements on the liquid contained in the containers, said non-destructive measuring apparatus being connected by the transfer system to the first redespatching means and to a direct supply station of the container storage means.

4. Analysis apparatus according to claim 3, further comprising means for recycling liquid remaining in the containers outside said analysis box and connected by the transfer system to the first redespatching means.

5. Analysis apparatus according to claim 4, wherein the transfer system comprises container switching means to alternatively direct the containers from the first container redespatching means to the recycling means and the non-destructive measuring apparatus and to alternatively direct the containers from the non-destructive measuring apparatus to the direct supply station and the recycling means.

6. Analysis apparatus according to claim 5, further comprising at least one manual analysis assembly outside said analysis box for performing manual analysis on the liquid contained in the containers, said manual analysis assembly having means for opening and closing the containers and second means for redespatching the containers to the transfer system.

7. Analysis apparatus according to claim 6, wherein said container switching means direct the containers from the first container redespatching means to the manual analysis assembly.

8. Analysis apparatus according to claim 7, wherein said manual analysis assembly also has means for washing and rinsing the containers.

\* \* \* \* \*

UNITED STATES PATENT AND TRADEMARK OFFICE
CERTIFICATE OF CORRECTION

PATENT NO. : 5,531,964
DATED : July 2, 1996
INVENTOR(S) : Joseph Besnier

It is certified that error appears in the above-indentified patent and that said Letters Patent is hereby corrected as shown below:

```
Column 2, lines 38, 54 and 66, delete "Jugs" and insert
         --jugs--.

Column 4, line 44, delete "Jug" and insert --jug--; and
         lines 57 & 63, delete "Jugs" and insert --jugs--

Column 6, lines 29 and 42, delete "Jugs" and insert --
         jugs--; and
         line 57, delete "Jug" and insert --jug--.

Column 7, line 10, delete "Jugs" and insert --jugs--.

Column 10, line 1 (Claim 8, line 1), delete "7" and insert
         --6--.
```

Signed and Sealed this

Twenty-fourth Day of December, 1996

Attest:

BRUCE LEHMAN

*Attesting Officer*  *Commissioner of Patents and Trademarks*